United States Patent [19]

Haag et al.

[11] 4,159,995
[45] Jul. 3, 1979

[54] CONVERSION OF SYNTHESIS GAS TO HYDROCARBON MIXTURES UTILIZING DUAL REACTORS

[75] Inventors: Werner O. Haag, Lawrenceville; Tracy J. Huang, Trenton, both of N.J.

[73] Assignee: Mobil Oil Corporation, New York, N.Y.

[21] Appl. No.: 826,487

[22] Filed: Aug. 22, 1977

[51] Int. Cl.$^2$ .................................................. C07C 1/04
[52] U.S. Cl. ............................. 260/450; 260/449.6 R; 260/449.6 M; 260/676 R; 260/668 R; 585/322; 585/243; 585/500
[58] Field of Search ................ 260/449.6 R, 449.6 M, 260/449 R, 449 M, 450, 673, 668, 676 R

[56] References Cited

U.S. PATENT DOCUMENTS

| | | | |
|---|---|---|---|
| 2,754,314 | 7/1956 | McGrath | 260/450 |
| 3,756,942 | 9/1973 | Cattarach | 260/673 |
| 3,760,024 | 9/1973 | Cattanch | 260/673 |
| 3,894,102 | 7/1975 | Chang et al. | 260/449 R X |
| 3,894,106 | 7/1975 | Chang et al. | 260/673 |
| 3,960,978 | 6/1976 | Givens | 260/673 |
| 3,972,958 | 8/1976 | Garwood et al. | 260/449.6 |
| 4,011,275 | 3/1977 | Zahner | 260/668 |
| 4,041,094 | 8/1977 | Kuo et al. | 260/449 R |
| 4,046,830 | 9/1977 | Kuo | 260/449 R |

FOREIGN PATENT DOCUMENTS 828228  10/1975  Belgium .................................. 260/449

Primary Examiner—Howard T. Mars
Attorney, Agent, or Firm—Charles A. Huggett; Carl D. Farnsworth

[57] ABSTRACT

A gaseous mixture of carbon monoxide and hydrogen is contacted in a first reactor with an iron Fischer-Tropsch catalyst such as potassium promoted iron under special conditions and the total products from said contact are then converted in a second reactor containing HZSM-5 to obtain either a highly olefinic or highly aromatic product depending on reaction conditions.

6 Claims, No Drawings

CONVERSION OF SYNTHESIS GAS TO HYDROCARBON MIXTURES UTILIZING DUAL REACTORS

BACKGROUND OF THE INVENTION

Field of the Invention

This invention is concerned with an improved process for converting synthesis gas, i.e. mixtures of gaseous carbon oxides with hydrogen or hydrogen donors, to hydrocarbon mixtures. In one aspect, this invention is particularly concerned with a process for converting synthesis gas substantially directly to hydrocarbon mixtures rich in aromatics.

Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. An excellent summary of the art of gas manufacture, including synthesis gas, from solid and liquid fuels, is given in *Encyclopedia of Chemical Technology*, Edited by Kirk-Othmer, Second Edition, Volume 10, pages 353–433, (1966), Interscience Publishers, New York, N.Y., the contents of which are herein incorporated by reference. The techniques for gasification of coal or other solid, liquid or gaseous fuel are not considered to be a part of this invention.

It is well known that synthesis gas comprising carbon monoxide and hydrogen will undergo conversion to form reduction products of carbon monoxide, at temperatures in the range of 300° F. to about 850° F. and pressures in the range of one to one thousand atmospheres pressure, over a fairly wide variety of catalysts. The Fischer-Tropsch proces, for example, which has been extensively studied, produces a range of hydrocarbons, waxy materials and some liquid materials which have been used as low octane gasoline. The types of catalysts that have been studied for this and related processes include those based on metals or oxides or iron, cobalt, nickel, ruthenium, thorium, rhodium and osmium.

The range of catalysts and catalyst modifications disclosed in the art encompass an equally wide range of conversion conditions for the reduction of carbon monoxide by hydrogen and provide considerable flexibility toward obtaining selected boiling-range products. Nonetheless, in spite of this flexibility, it has not been possible heretofore to provide a catalyst for medium pressure operation (5–30 atm) which will produce particularly olefin compositions comprising primarily beta double bond characteristics and boiling in the gasoline boiling range. A review of the status of this art is given in "Carbon Monoxide Hydrogen Reactions", *Encyclopedia of Chemical Technology*, Edited by Kirk-Othmer, Second Edition, Volume 4. pp. 446–488, Interscience Publishers, New York, N.Y.

The conversion of synthesis gas to hydrocarbon mixtures is disclosed in copending application Ser. No. 583,353, filed June 2, 1975 and copending application Ser. No. 566,167, filed Apr. 4, 1975. Compositions of iron, cobalt or nickel deposited in the inner absorption regions of crystalline zeolites are described in U.S. Pat. No. 3,013,990. Attempts to convert synthesis gas over X-zeolite base exchanged with iron, cobalt and nickel are described in Erdol and Kohle - Erdgas, Petrochemie; Brennstoff - chemie, Vol. 25, No. 4 pp. 187–188, April 1972.

One particularly desirable catalyst used in the conversion of syngas has been potassium promoted iron, which has been used in combination with special types of zeolites, such as ZSM-5 in order to produce valuable hydrocarbons. Thus, for example, copending Application Ser. No. 566.167 is directed towards the conversion of syngas with potassium promoted iron in admixture with HZSM-5. Although the process of this copending application is indeed effective in producing products having a substantial quantity of aromatics, nevertheless, there are disadvantages associated with said process, primarily in the regeneration aspect of the catalyst. It is known that when processes of this type are operated under conditions which favor the production of aromatics that there is also produced substantial amounts of coke which are deposited about the acid ZSM-5 catalyst. This requires that the catalyst be subjected to frequent regeneration, and due to the fact that the process of said copending application Ser. No. 566,167 involved a catalyst mixture containing an iron catalyst and a ZSM-5 catalyst, the extent and amount of regeneration was limited by the effect that the regeneration would have on the iron component. Thus, although HZSM-5 by itself exhibits a remarkable stability with regard to regeneration of the same by burning off carbon deposits, the same is not true with respect to a Fischer-Tropsch catalyst, in general, and iron promoted potassium in particular.

In Belgian Pat. No. 828,228 (1975) there is disclosed a process for the conversion of synthesis gas using a single stage process wherein the catalyst is a mixture of an iron containing Fischer-Tropsch catalyst and a ZSM-5 type zeolite. One of the examples however, is directed towards a two bed operation wherein syngas is contacted over a first bed containing an iron catalyst and the total product is thereafter contacted in a second bed containing a ZSM-5 type zeolite. The example resulted in poor aromatic production and excessive methane production.

In U.S. Pat. No. 4,046,830 there is disclosed a process wherein the total effluent from a Fischer-Tropsch operation is upgraded over a ZSM-5 type zeolite. Although the process of said patent is indeed a valuable one, it has been found that it can be significantly improved by operating within a narrow range of process conditions. Thus, the instant invention represents an improvement over U.S. Pat. No. 4,046,830.

BRIEF SUMMARY OF THE INVENTION

It has now been discovered that highly aromatic or highly olefinic gasoline of enhanced octane number can be produced by reacting synthesis gas, i.e. mixtures of hydrogen gas with gaseous carbon oxide or the equivalents of such mixtures utilizing a dual reactor conversion process. In the first reactor, the syngas mixture is reacted over an iron catalyst under certain reaction conditions. The product from this first stage conversion, without any separation of intermediates, is thereafter processed in a second reactor with an acidic zeolite such as HZSM-5 to yield a product wherein methane plus ethane is less than about 25 weight percent and the $C_5+$ gasoline fraction is at least 40 weight percent. The gasoline fraction has a boiling range of less than 400° F. at 90% overhead.

The process of this invention allows for a considerably greater flexibility with respect to both reaction conditions and the regeneration of the catalyst since separate reactors are used and each reactor can be operated at optimum conditions and each catalyst can be regenerated separately such that the process is capable of being operated at fairly long cycle times. As pointed out earlier, the coke which is deposited during the aromatizing reaction is deposited on the acidic zeolite, and in the novel process of this invention, this zeolite is remarkably stable during many regeneration cycles. On the other hand, the first reactor operation is carried out such that coke formation is not excessive and it also can be separately regenerated. It should be realized that optimum regeneration conditions for an iron catalyst are different from those necessary for an acidic catalyst.

DETAILED DESCRIPTION AND PREFERRED EMBODIMENTS

Synthesis gas as used in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, curde petroleum, shale oil, oil from tar sands, natural gas, as well as fuels derived from simple physical separations or more profound transformations of these materials, including coked coal, petroleum coke, gas oil, residue from petroleum distillation, and two or more of any of the foregoing materials in combination. Other carbonaceous fuels such as peat, wood and cellulosic waste materials also may be used.

The raw synthesis gas produced from fossil fuels will contain variou impurities such as particulates, sulfur, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention. However, it may not be necessary to remove substantially all the sulfur impurities when thoria is used as the carbon monoxide reducing component, since thoria is relatively little affected by sulfur compounds. Furthermore, should it be required, it is preferred to adjust the hydrogen-to-carbon oxides volume ratio to be within the range of from 0.2 to 6.0 prior to use in this invention. Should the purified synthesis gas be excessively rich in carbon oxides, it may be brought within the preferred range by the well known water-gas shift reaction. On the other hand, should the synthesis gas be excessively rich in hydrogen, it may be adjusted into the preferred range by the addition of carbon dioxide or carbon monoxide. Purified synthesis gas adjusted to contain a volume ratio of hydrogen-to-carbon oxides of from 0.2 to 6.0 will be referred to as adjusted synthesis gas.

It is contemplated that the synthesis gas for use in this invention includes art-recognized equivalents to the already-described mixtures of hydrogen gas with gaseous carbon oxides. Mixtures of carbon monoxide and steam, for example, or of carbon dioxide and hydrogen, to provide adjusted synthesis gas by in situ reaction, are contemplated.

The catalysts employed in the first reactor of this invention are conventional iron Fischer-Tropsch catalysts well known in the art. A preferred catalyst is potassium promoted iron Fe(K).

The crystalline aluminosilicate component used in the second reactor is a ZSM-5 type zeolite which is characterized by a pore dimension greater than about 5 Angstroms, i.e. it is capable of sorbing paraffins, and it has a silica-to-alumina ratio of at least 12, and a constraint index within the range of 1 to 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The zeolites utilized herein exhibit some unusual properties. They are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of stream even at high temperatures which induce irreversible collapse of the crystal framework of other zeolites, e.g. of the X and Z type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, an egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention have a silica to alumina ratio of at least about 12 and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "cpnstraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constant for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein as an inclusive rather than an exclusive value. That is, a zeolite when tested by any combination of conditions within the testing definition set forth hereinabove to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar materials. Recently issued U.S.Pat. No. 3,702,886 describing and claiming ZSM-5 is incorporated herein by reference.

ZSM-11 is more particularly described in United States Pat. No. 3,709,979, the entire contents of which are incorporated herein by reference.

ZSM-12 is more particularly described in U.S. Pat. No. 3,832,449, the entire centents of which are incorporated herein by reference.

United States Application Ser. No. 358,192, filed May 7, 1973, abandoned the entire contents of which are incorporated herein by reference, describes a zeolite composition, and a method of making such, designated as ZSM-21 which is useful in this invention. Recent evidence has been adduced which suggests that this composition of at least two (2) different zeolites, designated ZSM-35 and ZSM-38, one or both of which are the effective material insofar as the catalysis of this invention is concerned. Either or all of these zeolites is considered to be within the socpe of this invention. ZSM-35 is described in United States Application Serial Number 528,061, filed Nov. 29, 1974. ZSM-38 is described in U.S. application Ser. No. 528,060, filed Dec. 29, 1974 -abandoned.

The specific zeolites described, when prepared in the presence of organic cations, are substantially catalytically inactive, pssibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of aorganic cations in the forming solution may not be absolutely essential to the formation of this special type zeolite, however, the presence of these cations does appear to favor the formation of this special type of zeolite. More generally, it is desirable to activate this type zolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 in the acid form, i.e. H-ZSM-5 being particularly preferred.

In a preferred aspect of this invention, the initial zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given e.g. on page 19, of the article on "Zeolite Structure" by W. M. Meier. This paper, the entire contents of which are incorporated herein by reference, is included in "Proceedings of the Conference on Moleculer Sieves, London, April, 1967", published by the Society of Chemical industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of the catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

As has heretofore been stated the novel process of this invention does not reside merely in contacting syngas in a first reactor with an iron Fischer-Tropsch catalyst followed by contacting the total effluent in a second reactor over a ZSM-5 type catalyst, but rather, does reside in carrying out said operation under critical operating conditions.

One important criticality in the novel process of this invention resides in the temperature which is utilized in the first reactor and in this connection the temperature should be from about 450° F. to about 670° F. and preferably from 490° F. to 650° F. It has been found that operations at temperatures lower than those specified does not result in substantial conversion of syngas, whereas using temperatures higher than those specified results in excessive formation of methane and ethane. As has heretofore been pointed out, one of the objectives to the novel process of this invention is to provide a process wherein the methane plus ethane formation is less than 25 weight percent. Other operating parameters with regard to the first reactor are pressures from atmospheric to 1500 psig and peferably from 200 to 600 psig as well as weight hourly space velocities (WHSV) from 0.1 to 10 and preferably from 0.5 to 5.

The above-recited conditions with respect to the operations in the first reactor are absolutely critical in order to obtain the desired product of this invention. The abofe-defined reaction conditions assure a minimum production of methane plus ethane, i.e., less than 25 weight percent as well as a substantial conversion of carbon monoxide, i.e., greater than 50% and provide a product which can be upgraded in the section reactor with a high degree of efficiency.

The pressure utilized in the second reactor will be, in general, equal or less than that used in the first reactor, i.e., from atmospheric to 1500 psig. The space velocity in the second reactor will vary from 0.2 to 30 WHSV and more preferably from one to 12 WHSV. The second reactor temperature is from about 530° F. up to about 850° F. and more preferably from 550° F. to 800° F. In general, operation at temperatures from about 530–650 favor the formation of olefinic gasolien whereas temperatures from about 600° to 800° favor the production of aromatic gasolines, i.e. greater than 25 weight percent aromatics in the $C_5+$ fraction.

The following examples will illustrate the best mode contemplated for carrying out this invention.

EXAMPLE 1

The following example will illustrate the criticality of temperature in carrying out the novel process of this invention. Example 1a is an experiment within the operating parameters of this invention and Example 1b is the operation disclosed in Belgian Pat. No. 828,228. In each case the feed was a mixture of hydrogen and carbon monoxide having a $H_2/CO$ ratio of 1.0, the first reactor catalyst was FE(K) and the second reactor catalyst was HZSM-5. Specific operating conditions and the results obtained are set forth in the following table.

TABLE

| Example No. | 1a | 1b |
|---|---|---|
| Temp., (Avg.) First Reactor | 518° F. | 700° F. |
| Second Reactor | 650° F. | 700° F. |
| WHSV, First Reactor | 1.0 | 1.0 |
| Second Reactor | 1.8 | 1.4 |
| Pressure, psig | 400 | 250 |
| Conversion, wt % | | |

TABLE-continued

| Example No. | 1a | 1b |
|---|---|---|
| CO | 71 | 96.9 |
| $H_2$ | 70 | 76.9 |
| Wt % Hydrocarbon in Total Effluent | 18.1 | 25.6 |
| Hydrocarbon Distribution, wt % | | |
| $C_1 + C_2°$ | 11.7 | 61.6 |
| $C_3 + C_4$ | 45.8 | 29.6 |
| $C_5 +$ | 42.5 | 8.8 |
| Aromatics in $C_5 +$, wt % | 61.9 | 2.3 |
| Octane No. (R + O) of Liquid Product | 105.8 | |
| Boiling Range of Liquid Product 90% cut 387° F. | | |

The above example clearly demonstrates superior results which are obtained when operating within the critical parameters of the instant invention. Thus, Example 1a resulted in the production of a hydrocarbon product wherein the $C_5+$ fraction was greater than 40 weight percent and wherein the methane plus ethane make was less than 25 weight percent. As can be seen from the results obtained in accordance with Example 1b the methane and ethane produced was excessive and the $C_5+$ yield was only 8.8 weight percent.

EXAMPLES 2-4

In each of these examples a mixture of hydrogen, carbon monoxide and carbon dioxide in a ratio of 4.6 to 1 to 1.6 was used as the feed and in each example the catalyst in the first rector was Fe(K) and that in the second reactor was HZSM-5. A pressure of 400 psig was used in all examples in both the first and second rector.

Other operating conditions, as well as the results obtained are shown in the following table:

TABLE

| Example No. | 2 | 3 | 4 |
|---|---|---|---|
| Temp., (Avg.) First Reactor | 700° F. | 600° F. | 648° F. |
| Second Reactor | 700° F. | 600° F. | 804° F. |
| WHSV, First Reactor | 0.95 | 0.95 | 0.9 |
| Second Reactor | 9.80 | 9.80 | 9.8 |
| Conversion, wt % | | | |
| CO | 91.4 | 69.3 | 66.9 |
| $H_2$ | 34.9 | 36.2 | 38.0 |
| $CO_2$ | 25.1 | 1.7 | −0.3 |
| Total Effluent, wt % | | | |
| Hydrocarbon | 20.4 | 8.3 | 7.7 |
| $H_2$ | 5.6 | 5.4 | 5.2 |
| CO | 2.3 | 8.0 | 8.7 |
| $CO_2$ | 48.6 | 64.4 | 65.6 |
| $H_2O$ | 23.2 | 13.9 | 12.7 |
| Hydrocarbon Distribution, wt % | | | |
| $C_1$ | 30.9 | 12.1 | 13.3 |
| $C_2°$ | 5.5 | 1.9 | 3.4 |
| $C_2 =$ | — | 2.8 | 7.3 |
| $C_3°$ | 5.3 | 4.0 | 6.1 |
| $C_3 =$ | 0.9 | 2.9 | 9.8 |
| i-$C_4$ | 7.4 | 2.3 | 4.8 |
| n-$C_4$ | 4.8 | 2.6 | 3.8 |
| $C_4 =$ | 1.0 | 5.0 | 9.7 |
| i-$C_5$ | 4.9 | 2.5 | 3.6 |
| n-$C_5$ | 2.5 | 2.0 | 2.1 |
| $C_6 +$ non-arom. | 12.7 | 45.0 | 17.9 |
| Aromatics | 24.1 | 16.9 | 18.3 |
| $C_1 + C_2°$ in H.C., wt % | 36.4 | 16.8 | 16.7 |
| $C_3 + C_4$ in H.C., wt % | 19.4 | 16.8* | 31.5* |
| $C_5 +$ in H.C., wt % | 44.2 | 66.4 | 41.8 |
| Aromatics in $C_5 +$, wt % | 45.4 | 25.5 | 43.6 |

*Including $C_2 =$

From the above table it can be seen that Example 2 resulted in the production of an excessive amount of methane plus ethane, i.e., 36.4 weight percent, whereas the operations of Examples 3 and 4 resulted in acceptable methane plus ethane make while still yielding a $C_5+$ fraction of at least 40 weight percent, based on the hydrocarbons made.

The operation of Example 4 was carried out for 25 continuous days without regeneration of catalyst in either first or second reactor, thereby demonstrating catalyst stability. Although reaction conditions varied during the 25 days, the conditions set forth in the above table for Example 4 were achieved at least by the 24th day.

EXAMPLE 5-8

In each of these examples the feed utilized was a mixture of hydrogen, carbon monoxide in a ratio of 2:1 and the pressure in both the first and second reactors was 400 psig. The first reactor in all cases contained Fe(K) and the second reactor contained HZSM-5.

Other operating parameters and the results obtained are shown in the following table.

TABLE

| Example No. | 5 | 6 | 7 | 8 |
|---|---|---|---|---|
| Temp., (Avg.) First Reactor | 520° F. | 520° F. | 520° F. | 520° F. |
| Second Reactor | 520° F. | 550° F. | 650° F. | 850° F. |
| WHSV, First Reactor | 0.7 | → | → | 0.4 |
| Second Reactor | 1.2 | → | → | 0.8 |
| Conversion, wt % | | | | |
| CO | 66.4 | 77.6 | 79.4 | 94.8 |
| $H_2$ | 29.3 | 39.6 | 42.0 | 66.7 |
| Total Effluent, wt % | | | | |
| Hydrocarbon | 18.2 | 20.6 | 21.8 | 26.2 |
| $H_2$ | 9.6 | 8.2 | 7.8 | 4.5 |
| CO | 29.1 | 19.4 | 17.9 | 4.5 |
| $CO_2$ | 31.2 | 37.8 | 37.9 | 30.1 |
| $H_2O$ | 11.9 | 14.1 | 14.7 | 34.6 |
| Hydrocarbon Distribution, wt. % | | | | |
| $C_1$ | 14.9 | 11.6 | 11.4 | 17.3 |
| $C_2°$ | 6.1 | 3.7 | 4.2 | 7.4 |
| $C_2 =$ | 10.4 | — | — | — |
| $C_3°$ | 2.5 | 3.7 | 10.5 | 18.0 |
| $C_3 =$ | 5.1 | 0.9 | — | 0.1 |
| i-$C_4$ | 0.3 | 2.7 | 12.8 | 10.7 |
| n-$C_4$ | 2.8 | 5.8 | 9.1 | 6.9 |
| $C_4 =$ | 3.0 | 2.1 | — | — |
| i-$C_5$ | 1.7 | 3.2 | 9.6 | 5.2 |
| n-$C_5$ | 1.4 | 4.4 | 5.0 | 1.4 |
| $C_6 +$ non-arom. | 51.9 | 46.8 | 14.0 | 2.9 |
| Aromatics | | 15.2 | 23.5 | 30.1 |
| $C_1 + C_2°$ in H.C., wt % | 21.0 | 15.3 | 15.6 | 24.7 |
| $C_3 + C_4$ in H.C., wt % | 24.0* | 15.2 | 32.3 | 35.7 |
| $C_5 +$ in H.C., wt % | 55.0 | 69.6 | 52.0 | 39.6 |
| Aromatics in $C_5 +$, wt % | — | 21.8 | 45.1 | 76.0 |
| Boiling Range of Liquid Product 90% cut, ° F. | 427 | 381 | 344 | 365 |

*Including $C_2 =$

As can be seen, operations in accordance with Example 5 did not produce a desired product since the boiling range of the material was 427° at 90 percent overhead. As can be seen, the second reactor temperature of Example 5 was 520° F. which is outside the scope of the instant invention. Example 6 and 7 did produce very excellent results as can be seen from the data listed in the above table.

EXAMPLES 9-13

The procedure of Examples 5-8 was repeated with the exception that the HZSM-5 zeolite used in the second reactor had an α-value of sixteen. The α-value of the HZSM-5 utilized in Examples 5-8 was 200.

The α-value is a measure of the hexane cracking activity of the catalyst and is to be determined in accordance with the method set forth by P. B. Weisz and J. N. Miale in "Journal of Catalysis", Vol. 4, No. 4, August 1965, pp. 527–529, which description is herein incorporated by reference; except that the temperature of the α-measurement is 1000° F. Lower α-values than about 200 were obtained by steam treating the catalyst at elevated temperature.

Specific operating conditions as well as the results obtained are shown in the following tables.

TABLE

| Example No. | 9 | 10 | 11 | 12 | 13 |
|---|---|---|---|---|---|
| Temp., (Avg.) ° F. First Reactor | 520 | 520 | 520 | 530 | 600 |
| Second Reactor | 550 | 590 | 620 | 650 | 650 |
| WHSV, First Reactor | 0.7 | → | → | → | → |
| Second Reactor | 1.3 | → | → | → | → |
| Conversion, wt % | | | | | |
| CO | 77.9 | 76.8 | 79.1 | 81.6 | 93.2 |
| $H_2$ | 32.6 | 21.0 | 29.9 | 31.5 | 51.0 |
| Total Effluent, wt % | | | | | |
| Hydrocarbon | 17.8 | 20.5 | 20.1 | 21.0 | 25.0 |
| $H_2$ | 8.3 | 9.7 | 8.6 | 8.4 | 5.9 |
| CO | 19.4 | 20.3 | 18.3 | 16.2 | 6.0 |
| $CO_2$ | 42.4 | 36.7 | 40.8 | 42.8 | 49.1 |
| $H_2O$ | 12.2 | 12.8 | 12.2 | 11.6 | 14.0 |
| Hydrocarbon Distribution, wt % | | | | | |
| $C_1$ | 14.0 | 14.1 | 12.0 | 13.2 | 13.2 |
| $C_2°$ | 3.6 | 4.1 | 4.0 | 4.6 | 3.9 |
| $C_2=$ | 4.2 | 3.5 | 2.3 | — | — |
| $C_3°$ | 3.0 | 3.0 | 3.2 | 5.6 | 7.4 |
| $C_3=$ | 7.6 | 2.9 | 2.0 | 0.9 | 1.2 |
| $i\text{-}C_4$ | 0.4 | 1.0 | 2.9 | 8.4 | 6.3 |
| $n\text{-}C_4$ | 3.2 | 3.1 | 4.0 | 6.3 | 4.9 |
| $C_4=$ | 4.2 | 7.4 | 5.8 | 1.1 | 1.5 |
| $i\text{-}C_5$ | 1.4 | 1.6 | 3.3 | 6.8 | 5.3 |
| $n\text{-}C_5$ | 1.4 | 1.9 | 3.1 | 5.0 | 3.7 |
| $C_6$ + non-arom. | 57.2 | 57.5 | 51.9 | 32.0 | 35.9 |
| Aromatics | | | 5.4 | 16.1 | 16.8 |
| $C_1 + C_2°$ in H.C., wt % | 17.6 | 18.2 | 16.0 | 17.8 | 17.1 |
| $C_3 + C_4$ in H.C., wt % | 22.5* | 20.9* | 20.3* | 22.3 | 21.2 |
| $C_5$ + in H.C., wt % | 59.9 | 60.9 | 63.7 | 59.9 | 61.7 |
| Aromatics in $C_5$ +, wt % | — | — | 8.5 | 26.8 | 27.3 |
| Octane No. (R + O) of Liquid Product | 90.0 | 86.9 | 86.9 | 84.7 | 87.1 |
| Boiling Range of Liquid Product 90% cut, ° F. | 398 | 383 | 361 | 358 | 359 |

*Including $C_2=$

As will be seen, operations in accordance with Examples 9—13 resulted in the production of a desired product in excellent yields with very acceptable methane plus ethane make.

Examples 9, 10, 11, 12 and 13 were run continuously for 4, 7, 8, 21 and 38 days respectively. Operating conditions may have varied for each example, but the conditions set forth in the above table were achieved at least by the last day.

EXAMPLES 14–18

The procedure of Example 2–4 was repeated with the exception that the HZSM-5 had an alpha value of about 66.

The results are shown below:

TABLE

| Example No. | 14 | 15 | 16 | 17 | 18 |
|---|---|---|---|---|---|
| Temp., (Avg.) ° F. First Reactor | 600 | 600 | 626 | 644 | 648 |
| Second Reactor | 580 | 600 | 644 | 739 | 804 |
| WHSV, First Reactor | 1.0 | → | → | → | → |
| Second Reactor | 9.9 | → | → | → | → |
| Conversion, wt % | | | | | |
| CO | 68.9 | 69.3 | 70.6 | 65.3 | 66.9 |
| $H_2$ | 34.8 | 36.2 | 38.7 | 37.9 | 38.0 |
| $CO_2$ | 0.4 | 1.7 | −3.5 | −1.8 | −0.3 |
| Total Effluent, wt % | | | | | |
| Hydrocarbon | 7.7 | 8.3 | 7.0 | 7.1 | 7.7 |
| $H_2$ | 5.5 | 5.4 | 5.2 | 5.2 | 5.2 |
| CO | 8.1 | 8.0 | 7.7 | 9.1 | 8.7 |
| $CO_2$ | 65.2 | 64.4 | 67.7 | 66.6 | 65.6 |
| $H_2O$ | 13.4 | 13.9 | 12.4 | 12.1 | 12.8 |
| Hydrocarbon Distribution, wt % | | | | | |
| $C_1$ | 12.1 | 12.1 | 12.1 | 13.6 | 13.3 |
| $C_2°$ | 2.5 | 1.9 | 2.3 | 2.6 | 3.4 |
| $C_2=$ | 5.0 | 2.8 | 4.0 | 6.1 | 7.3 |
| $C_3°$ | 2.7 | 4.0 | 1.9 | 2.1 | 6.1 |
| $C_3=$ | 3.0 | 2.9 | 4.1 | 9.2 | 9.8 |
| $i\text{-}C_4$ | 2.3 | 2.3 | 2.7 | 2.1 | 4.8 |
| $n\text{-}C_4$ | 3.0 | 2.6 | 2.3 | 2.3 | 3.8 |
| $C_4=$ | 6.9 | 5.0 | 8.5 | 14.5 | 9.7 |
| $i\text{-}C_5$ | 1.3 | 2.5 | 2.7 | 1.1 | 3.6 |
| $n\text{-}C_5$ | 1.0 | 2.0 | 0.6 | 0.7 | 2.1 |
| $C_6$ + non-arom. | 48.6 | 45.0 | 41.5 | 30.6 | 17.9 |
| Aromatics | 11.6 | 16.9 | 17.5 | 15.0 | 18.3 |
| $C_1 + C_2°$ in H.C., wt % | 14.6 | 14.0 | 14.3 | 16.2 | 16.7 |
| $C_3 + C_4$ in H.C., wt % | 23.9* | 19.6* | 23.5* | 36.3* | 31.5* |
| $C_5$ + in H.C., wt % | 62.5 | 66.4 | 62.2 | 47.5 | 41.8 |
| Aromatics in $C_5$ +, wt % | 18.6 | 25.5 | 28.1 | 31.7 | 43.6 |
| Octane No. (R + O) of Liquid Product | 91.0 | 90.1 | 92.1 | 93.0 | |
| Boiling Range of Liquid Product 90% cut, ° F. | | | 374 | 385 | |

*Including $C_2=$

EXAMPLES 19 AND 20

The procedure of Examples 14–18 were repeated with the following exceptions:
(a) The ratio feed of $H_2:CO:CO_2$ was 5.8:1.0:1.3.
(b) The α-value of HZSM-5 in Example 19 was 16. The α-value of HZSM-5 in Example 20 was 66.
(c) The operating conditions and results obtained are shown below.

TABLE

| Example No. | 19 | 20 |
|---|---|---|
| Temp., (Avg.) °F. First Reactor | 600 | 600 |
| Second Reactor | 650 | 680 |
| WHSV, First Reactor | 0.74 | 0.76 |
| Second Reactor | 1.36 | 7.82 |
| Conversion, wt % | | |
| CO | 90.3 | 89.9 |
| $H_2$ | 45.1 | 40.3 |
| $CO_2$ | 3.9 | 14.0 |
| Total Effluent, wt % | | |
| Hydrocarbon | 13.4 | 15.6 |
| $H_2$ | 6.7 | 7.2 |
| CO | 2.8 | 3.0 |
| $CO_2$ | 56.3 | 50.4 |
| $H_2O$ | 20.8 | 23.7 |
| Hydrocarbon Distribution, wt % | | |
| $C_1$ | 19.3 | 14.0 |
| $C_2°$ | 5.4 | 2.8 |
| $C_2=$ | — | — |
| $C_3°$ | 6.0 | 5.0 |
| $C_3=$ | 0.5 | 1.1 |
| $i\text{-}C_4$ | 9.5 | 10.6 |
| $n\text{-}C_4$ | 5.5 | 5.7 |
| $C_4=$ | — | 1.1 |
| $i\text{-}C_5$ | 7.2 | 7.8 |
| $n\text{-}C_5$ | 3.1 | 3.8 |
| $C_6$ + non-arom. | 20.4 | 20.8 |
| Aromatics | 23.1 | 27.2 |
| $C_1 + C_2°$ in H.C., wt % | 24.7 | 16.8 |
| $C_3 + C_4$ in H.C., wt % | 21.5 | 23.5 |
| $C_5$ + in H.C., wt % | 53.9 | 59.7 |
| Aromatics in $C_5$ +, wt % | 42.9 | 45.6 |
| Octane No. (R + O) of Liquid Product | 87 | 95.0 |
| Boiling Range of Liquid Product 90% cut, °F. | 366 | 359 |

As can be seen, excellent results were obtained.
What is claimed is:

1. In a process for converting synthesis gas comprising carbon monoxide and hydrogen to gasoline boiling components wherein synthesis gas is contacted in a first reactor under conditions of elevated temperatures and pressure with an iron containing Fishcher-Tropsch catalyst and the total product from said first reactor is passed to a second reactor containing an acidic crystalline zeolite having a pore diameter greater than about five Angstroms, a silica to alumina ratio of at least 12, a crystal density substantially below 1.6 grams per cubic centimter and a constraint index of from 1 to 12 the improvement which comprises:
   - (a) carrying out said contact in said first reactor at a temperature of from 450° to 670° F., a pressure of from atmospheric to 1500 psig and a weight hourly space velocity of from 0.1 to 10.
   - (b) operating said second reactor at a temperature of from 530° F. to about 850° F., a pressure of from atmospheric to about 1500 psig and at a weight hourly space velocity of from 0.2-30, and
   - (c) recovering a $C_5+$ gasoline fraction in a yield of at least 40 weight percent based on the total hydrocarbons produced, said gasoline fraction having a boiling range of less than 400° F. at a 90% overhead, and
   - (d) producing methane plus ethane in a amount no greater than 25 weight percent.

2. The process of claim 1 wherein the temperature of the first reactor is from about 490° F. to about 650° F.

3. The process of claim 2 wherein the temperature of the second reactor is from about 550° F. to about 800° F.

4. The process of claim 2 wherein the catalyst in the first reactor is potassium promoted iron and the zeolite in the second reactor is HZSM-5.

5. The process of claim 3 wherein the catalyst in the first reactor is potassium promoted iron and the catalyst in the second reactor is HZSM-5.

6. The process of claim 1 wherein the temperature of the second reactor is from 600°–800° F. and the $C_5+$ gasoline fraction produced has an aromatic content greater than 25 weight percent.

* * * * *

UNITED STATES PATENT AND TRADEMARK OFFICE
CERTIFICATE OF CORRECTION

PATENT NO. : 4,159,995

DATED : July 3, 1979

INVENTOR(S) : WERNER O. HAAG and TRACY J. HUANG

It is certified that error appears in the above-identified patent and that said Letters Patent are hereby corrected as shown below:

| | |
|---|---|
| Column 1, line 37 | "proces" should be --process--. |
| Column 3, line 30 | "curde" should be --crude--. |
| Column 4, line 35 | "Z type" should be --A type--. |
| Column 5, line 23 | "cpnstraint" should be --constraint--. |
| Column 6, line 51 | "socpe" should be --scope--. |
| Column 6, line 58 | "pssibly" should be --possibly--. |
| Column 6, line 63 | "aorganic" should be --organic--. |
| Column 8, line 28 | "abofe" should be --above--. |
| Column 8, line 32 | "section" should be --second--. |
| Column 8, line 42 | "gasolien" should be --gasoline--. |
| Column 9 (Table), line 13 | "387°F" should be under the 1a column. |
| Column 9, line 33 | "rector" should be --reactor--. |
| Column 13, line 5 | "Fishcher-Tropsch" should be --Fischer-Tropsch-- |
| Column 13, line 11 | "centimter" should be --centimeter--. |

Signed and Sealed this

Twenty-seventh Day of November 1979

[SEAL]

Attest:

RUTH C. MASON
*Attesting Officer*

LUTRELLE F. PARKER
*Acting Commissioner of Patents and Trademarks*